Figure 1:
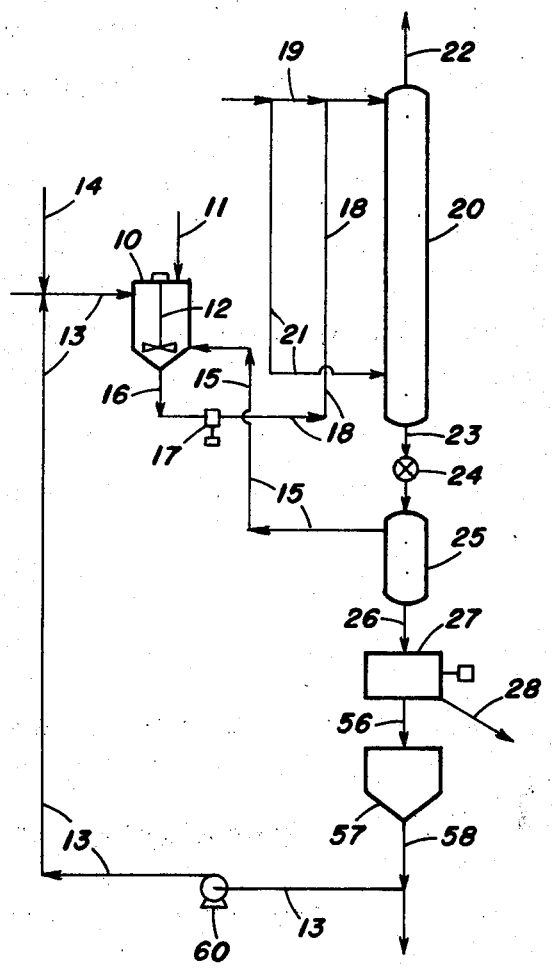

United States Patent [19]
Sze et al.

[11] 3,968,152
[45] July 6, 1976

[54] PRODUCTION OF AROMATIC CARBOXYLIC ACIDS

[75] Inventors: Morgan C. Sze, Upper Montclair; Daniel H. Gold, Plainfield; Richard T. Whitehead, Westfield, all of N.J.

[73] Assignee: The Lummus Company, Bloomfield, N.J.

[22] Filed: Jan. 31, 1975

[21] Appl. No.: 545,793

Related U.S. Application Data

[63] Continuation of Ser. No. 295,512, Oct. 6, 1972, abandoned, which is a continuation-in-part of Ser. No. 713,931, March 18, 1968, abandoned.

[52] U.S. Cl. ............................................ 260/515 P
[51] Int. Cl.² ................... C07C 63/24; C07C 63/26
[58] Field of Search ................................. 260/515 P

[56] References Cited

UNITED STATES PATENTS

| | | | |
|---|---|---|---|
| 2,979,526 | 4/1961 | Gasson et al. | 260/515 |
| 3,031,500 | 4/1962 | Gasson et al. | 260/515 |

*Primary Examiner*—James A. Patten
*Attorney, Agent, or Firm*—Marn & Jangarathis

[57] ABSTRACT

Aromatic mono- and polycarboxylic acids are produced by hydrolyzing the corresponding mono- and polynitriles in aqueous slurry containing a catalyst, removing ammonia from the hydrolysis mixture by countercurrent stripping with steam, and cooling the hydrolysis product to separate the carboxylic acid.

10 Claims, 2 Drawing Figures

PRODUCTION OF AROMATIC CARBOXYLIC ACIDS

RELATED APPLICATIONS

This is a continuation of application Ser. No. 295,512, filed Oct. 6, 1972, which in turn is a continuation - in part of application Ser. No. 713,931, filed by us Mar. 18, 1968, both now abandoned.

BACKGROUND AND PRIOR ART

This invention relates to the production of aromatic mono- and polycarboxylic acids and, more specifically, to the hydrolysis of aromatic mono- and polynitriles to the corresponding aromatic mono- and polycarboxylic acids in a novel operation.

Catalytic conversion of aromatic hydrocarbons to aromatic polynitriles, as xylenes to benzodinitriles, is known. Suitable conversions are described in U.S. Pat. No. 3,479,385, for example. Hydrolysis of the benzodinitriles to the corresponding benzene dicarboxylic acids has also been described in application Ser. No. 551,013, filed May 18, 1966. By integrating the catalytic conversion and the hydrolysis process, it is possible to prepare a polynitrile, purify and then hydrolyze the latter by hydrolysis. For example, p-xylene is converted to terephthalonitrile which is then purified and the purified nitrile is subjected to hydrolysis. Terephthalic acid is recovered from the resulting hydrolysis product for use in the manufacture of resins and fibers.

The overall reaction involved in hydrolysis of terephthalonitrile is:

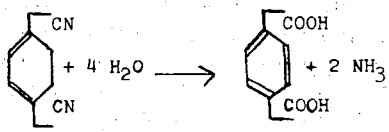

Processes presently in use for hydrolyzing nitriles to the corresponding acids are carried out in two steps. First, the nitrile is partially hydrolyzed to a salt, ester, or amide, which is then converted, by hydrolysis or other means, to the carboxylic acid. Such processes can be costly to use because they require two sets of hydrolyzing equipment, including vessels, pipes, instruments, etc. For example, see U.S. Pat. Nos. 2,979,526 and 3,031,500 of Gasson, et al.

In accordance with the present invention, there is provided a single-step process for the production of an aromatic mono- or polycarboxylic acid by hydrolysis of its corresponding aromatic mono- or polynitrile, which comprises maintaining an aqueous slurry containing the aromatic nitrile, water and a minor amount of a catalyst selected from the group consisting of alkali and alkaline earth metal hydroxides, carbonates and salts of the aromatic carboxylic acids, and ammonium salts of said acids, at a temperature of from about 300°F to about 600°F for a sufficient time interval to hydrolyze substantially all of the aromatic nitrile to a hydrolysis product thereof containing the aromatic carboxylic acid and partially hydrolyzed aromatic nitrile and stripping ammonia from the hydrolysis product by contacting the product countercurrently with steam. The product is then cooled to a temperature of from about 100°F to about 300°F, whereupon the aromatic carboxylic acid precipitates out. The alkali metal, alkaline earth metal and ammonium salts of aromatic mono- and polycarboxylic acids are effective catalysts for the hydrolysis of the nitriles to the corresponding acids.

The process of this invention permits production of carboxylic acids from nitriles using less equipment than was heretofore required. Consequently, the utility requirements are also lowered.

Figure 2:
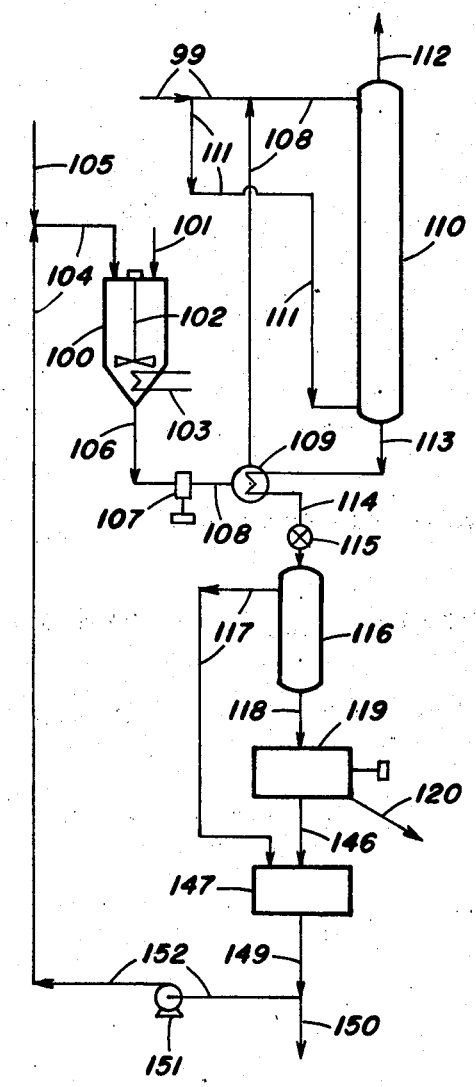

Illustrations of the invention are given in the accompanying drawings in which FIGS. 1 and 2 are simplified flow diagrams for the hydrolysis of terephthalonitrile to terephthalic acid and for recovery of the latter.

Referring now to FIG. 1, which depicts a preferred embodiment of the invention, as used for producing terephthalic acid of high purity, terephthalonitrile which is substantially free from impurities, particularly hydrocarbons, aromatic and aliphatic mononitriles and dinitriles, ketones, alcohols and aliphatic acids, is passed into slurry tank 10 from line 11. Tank 10 is equipped with agitator 12. Water containing a minor amount of catalyst such as dipotassium terephthalate in line 13, from a process source described hereinafter, is passed into slurry tank 10. Fresh or make-up catalyst solution can also be added to line 13 from line 14. A slurry of terephthalonitrile, water and catalyst is formed in tank 10 and is heated therein to approximately 200°F. Steam from line 15 is passed into tank 10 and serves to provide heat for the slurry.

The heated slurry is removed from tank 10 through line 16, reciprocating pump 17 and line 18 wherein it is combined with steam at approximately 430 psia in line 19 to raise the temperature of the slurry to the desired hydrolysis temperature, as about 395°F, and thence is passed into hydrolyzer 20. In practice, temperatures ranging from about 300°F to about 600°F are employed, with preference given to temperatures of 350°–540°F.

Pressure in hydrolyzer 20 is determined by the temperature of the liquid at the top thereof and by the partial pressure of the ammonia which is evolved during hydrolysis. Typical pressures range from 100–2000 psia.

In hydrolyzer 20, terephthalonitrile is converted to terephthalic acid, the degree of conversion being dependent upon the temperature therein, the residence time and the catalyst used. Such operating variables are discussed in detail hereinafter. In this illustration the potassium cation concentration in the charge to hydrolyzer 20 is about 5 moles per 100 moles of nitrile group of the terephthalonitrile charge, and residence time is about 6 hours.

In a continuous process, the catalytic cation combines with the acids formed in hydrolyzer 20 to form the corresponding salts. Thus, with potassium carbonate used initially as a catalyst, the potassium forms other salts in the process and is recycled in the form of the potassium salts of terephthalic acid and of terephthalamic acid. It is advantageous to hydrolyze only a substantial portion of the terephthalonitrile to terephthalic acid; in such case, a lower conversion is realized, but available for recycle as catalysts are the potassium salts of terephthalic acid or terephthalamic acid and the ammonium salts of the same acids together with terephthalamide. Ammonium salts of terephthalic acid and terephthalamic acid also act as catalysts in the hydrolysis of aromatic mono- and polynitriles to their corresponding acids.

Ammonia is stripped from the hydrolysis mixture by steam added through line 21 and passed countercurrent to the mixture, and is removed from hydrolyzer 20 through overhead line 22. The ammonia can be charged, for example, to a reactor (not shown) with p-xylene for the production of terephthalonitrile.

Terephthalic acid, formed by hydrolysis in hydrolyzer 20, is removed as a slurry together with other hydrolysis products through line 23, controlled by valve 24 therein, to flash vessel 25. Steam is removed from vessel 25 through line 15. As steam is flashed from the hydrolysis products, the temperature thereof is lowered to about 240°F.

The cooled hydrolysis products are passed from vessel 25 through line 26 to centrifuge 27. In the centrifuge, terephthalic acid is separated from materials in solution in the hydrolysis products, and removed via line 28.

The aqueous materials separated in centrifuge 27 are passed through line 56 to receiver 57. They are removed from the latter through discharge line 58, from which a portion can be removed through purge line 59. The balance in line 58 is pumped via pump 60 in line 13 to slurry tank 10.

The process described will produce aromatic carboxylic acids which, in most cases will be sufficiently pure for use as produced. However, certain acids, such as those used in producing fibers, especially terephthalic acid, will require further purification before commercial use. The impurities present in the acid after removal from centrifuge 27 will comprise mainly nitrogenous partially hydrolyzed products of the starting nitrile. In the case of terephthalic acid these are believed to consist primarily of terephthalamide and terephthalamic acid. Specifications for terephthalic acid for use in producing polyester fibers require a nitrogen content of below 20 ppm. Similar low nitrogenous content is required of other acids useful in fiber manufacture, such as pyromellitic acid.

If purification is required, it can be performed according to various schemes. Most advantageously, the aromatic carboxylic acid is purified by one or more subsequent aqueous hydrolysis treatments at elevated temperature and pressure, to complete the hydrolysis of the impurities, as disclosed in U.S. Pat. applications Ser. No. 178,263, now U.S. Pat. No. 3,776,949 (12-4-73), and 178,382, now U.S. Pat. No. 3,833,647 (9-3-74), assigned to the assignee hereof.

A typical example in which the process sequence is as shown by FIG. 1, is given below. All quantities are expressed in moles per hour, except as otherwise specified. Terephthalonitrile is abbreviated to "TPN," terephthalic acid to "TPA" for convenience.

EXAMPLE 1

| | |
|---|---:|
| Fresh Charge to Slurry Tank 10 | |
|    TPN, line 11 | 75.3 |
| Feed to Primary Hydrolyzer 20 | |
|    Water, line 13 | 1869.6 |
|    TPA, line 13 | 0.1 |
|    Diammonium terephthalate, line 13 | 20.3 |
|    Monoammonium terephthalamate, line 13 | 2.3 |
|    Dipotassium terephthalate, line 13 | 3.0 |
|    Monopotassium terephthalamate, line 13 | 6.8 |
|    TPN | 75.3 |
| Steam to Hydrolyzer 20 | |
|    Charge, line 18 | 414.1 |
|    Stripping, line 21 | 95.9 |
| Hydrolyzer (20) overhead in Line 22 | |
|    Ammonia | 150.6 |
|    Water | 361.7 |
| Water Reacted in Hydrolyzer (20) | 301.2 |
| Hydrolyzer (20) Product in Line 23 | |
|    TPA | 75.4 |
|    Diammonium terephthalate | 20.3 |
|    Monoammonium terephthalamate | 2.3 |
| -continued | |
|    Dipotassium terephthalate | 3.0 |
|    Monopotassium terephthalamate | 6.8 |
|    Water | 1302.6 |
| Centrifuge (27) Product in Line 28 | |
|    TPA | 75.3 |
|    Water | 462.9 |
| Centrifuged Solution in Line 56 | |
|    TPA | 0.1 |
|    Diammonium terephthalate | 20.3 |
|    Monoammonium terephthalamate | 2.3 |
|    Dipotassium terephthalate | 3.0 |
|    Monopotassium terephthalamate | 6.8 |
|    Water | 1188.4 |
| Primary Flash Vapor in Line 15 | 267.2 |

Thus, there is essentially mole per mole conversion of terephthalonitrile to terephthalic acid.

FIG. 2 illustrates a modified process operation, one wherein higher hydrolysis temperatures are employed. Since many features of FIG. 2 are the same as those of FIG. 1, only the modifications are described in detail in the interests of brevity. Slurry tank 100 receives terephthalonitrile from line 101. Tank 100 is equipped with stirrer 102 and with steam coil 103 which provides heat to the contents of the tank. Water and catalyst recycled in the process are delivered to tank 100 from line 104. Make-up water and catalyst can be added to line 104 via line 105.

Heated slurry is passed from tank 100 through line 106, reciprocating pump 107 and line 108 in which is located heat exchanger 109. In passing through heat exchanger 109, the slurry is heated from about 260°F to about 460°F. High pressure saturated steam, 885 psia and 530°F, in line 99 is added to line 108, such that the slurry and steam therein are passed together into hydrolyzer 110. Hydrolysis of the terephthalonitrile occurs in hydrolyzer 110, at about 500°F, 800 psia and a residence time of about 6 hours. Ammonia is stripped from the hydrolysis products by additional steam taken from line 99 through line 111, and contacted countercurrently with the hydrolysis products and is removed from hydrolyzer 110 through line 112.

The balance of the hydrolysis products are passed from hydrolyzer 110 through discharge line 113 to heat exchanger 109 wherein heat is extracted. The hydrolysis products are then passed through line 114, controlled by valve 115, to flash vessel 116. Steam is removed in vessel 116 through line 117, the temperature of the remaining hydrolysis products being lowered thereby to about 210°–220°F. The cooler hydrolysis products are passed through line 118 to centrifuge 119, wherein terephthalic acid is separated from other products. Terephthalic acid is removed in line 120.

Aqueous materials separated in centrifuge 119 are passed through line 146 to tank 147, wherein they are combined with steam in line 117 flashed from vessel 116 and with steam in line 148. The aqueous mixture in tank 147 is removed through line 149; a portion thereof can be purged through line 150 and the balance can be pumped by pump 151 in line 152 to line 104.

The operations shown in FIG. 2 are illustrated by the following typical example.

EXAMPLE 2

| | |
|---|---:|
| Fresh Charge to Slurry Tank 100 | |
|    TPN, line 101 | 75.3 |
| Feed to Primary Hydrolyzer 110 | |
|    Water, line 104 | 5144.9 |
|    TPA, line 104 | 0.1 |
|    Monosodium terephthalamide, line 104 | 3.8 |
|    Disodium terephthalate, line 104 | 1.9 |

-continued

| | |
|---|---|
| Terephthalamide, line 104 | 0.8 |
| TPN | 75.3 |
| Steam to Hydrolyzer 110 | |
| Charge, line 108 | 298.4 |
| Stripping, line 111 | 79.4 |
| Hydrolyzer (110) Overhead in line 112 | |
| Ammonia | 150.6 |
| Water | 853.4 |
| Water Reacted in Hydrolyzer 110 | 301.2 |
| Hydrolyzer (110) Product in Line 113 | |
| TPA | 75.4 |
| Disodium terephthalate | 1.9 |
| Monosodium terephthalamate | 3.8 |
| Terephthalamide | 0.8 |
| Water | 3990.3 |
| Centrifuge (119) Product in Line 120 | |
| TPA | 75.3 |
| Water | 462.9 |
| Centrifuged Solution in Line 146 | |
| TPA | 0.1 |
| Disodium terephthalate | 1.9 |
| Monosodium terephthalamate | 3.8 |
| Terephthalamide | 0.8 |
| Water | 3527.4 |

Here again, there is essentially mole per mole conversion of terephthalonitrile to terephthalic acid.

While the process illustrated by FIG. 2 is effective for the purpose of efficiently obtaining terephthalic acid of a high degree of purity, the process illustrated by FIG. 1 is preferred. Thus, the hydrolysis of terephthalonitrile can be conducted at lower temperatures, lower pressures and with higher terephthalonitrile concentrations then shown with FIG. 2. By operating at such temperatures, pressures, and concentrations, the initial hydrolyzer (e.g., 20) can be smaller in size and less expensive than that required in connection with FIG. 2.

The invention is illustrated above by the conversion of terephthalonitrile to terephthalic acid. It is to be understood, however, that the invention can also be employed for the hydrolysis of other aromatic mono- and polynitriles to their corresponding aromatic mono- and polycarboxylic acids. For example, the following hydrolysis can be effected: benzonitrile to benzoic acid; tolunitrile to toluic acid; o-phthalonitrile to phthalic acid; isophthalonitrile to isophthalic acid; p-cyanobenzamide to terephthalamic acid, and 1,2,4-benzenetrinitrile to trimellitic acid.

It is of particular significance that, by use of this process, aromatic polycarboxylic acids having at least one pair of carboxyl groups attached to adjacent carbon atoms in the aromatic ring, can be prepared via the corresponding nitriles. Phthalic acid, trimellitic acid, and pyromellitic acid (1,2,4,5-benzenetetracarboxylic acid) are the most important, commercially, of such acids. These acids are currently prepared by oxidation of the corresponding methylbenzenes, either directly or through the anhydride. Separation of by-products of the oxidation reaction is often expensive and difficult. These acids cannot be effectively produced via the ammonium salts in a two-stage process such as that of the Gasson, et al patents because heating of the ammonium salts will tend to result in formation of the imide (or di-imide) e.g., phthalimide, rather than the acid or anhydride.

The nitrile charged in the process can be pure or can be contaminated with other materials which are formed in the preparation of the nitrile. However, it will be recognized that more efficient operation is realized with a nitrile charge substantially free of contaminants.

As indicated, catalysts employed in the hydrolysis are alkali or alkaline earth metal hydroxides, carbonates and salts of the aromatic mono- or polycarboxylic acids formed in the hydrolysis and ammonium salts of said acids. The catalytic cation concentration is about 1 to about 30, preferably 2–10 moles per 100 moles of functional nitrile group in the charge.

Temperatures maintained in hydrolysis vary from about 300°F to about 600°F, with a preferred range being 350°–540°F.

Pressures in the hydrolyzer range from about 100 to about 2000 psia.

Residence time the hydrolysis ranges from about 1 to about 10 hours, preferably 6 hours.

It has been found desirable to hydrolyze only a substantial portion of the nitrile to the corresponding acid, whether or not subsequent purification is to be effected. Since the nitrogen-containing impurities, such as amides and terephthalamic acid, are soluble in water whereas terephthalic acid is not, the acid recovered after centrifuging and washing will be substantially pure and will be suitable for most uses, except when an extremely pure acid is required. The wash water, containing the nitrogen-containing impurities and salts of the acid is recycled back to the hydrolyzer.

Many modifications and variations of the invention as set forth above can be made without departing from the spirit and scope thereof. Consequently, the appended claims are intended to include such modifications and variations.

We claim:

1. A continuous process for the production of an aromatic carboxylic acid by hydrolysis of its corresponding aromatic nitrile, comprising:

continuously introducing an aqueous slurry, containing the aromatic nitrile, water and a minor amount of a catalyst is at least one member selected from the group consisting of hydroxides and carbonates of the alkali and alkaline earth metals and the alkali, alkaline earth and ammonium salts of aromatic carboxylic acids, into an upper portion of a reactor;

maintaining the slurry at a temperature of from 300°F to 600°F for a period of from 1 to 10 hours, while continuously simultaneously stripping ammonia from the aqueous reaction mixture by continuously introducing steam into a lower portion of the reactor;

continuously removing ammonia as overhead from the reactor;

continuously removing an aqueous hydrolysis effluent from a lower portion of the reactor;

cooling the aqueous hydrolysis effluent to temperature of from about 100°F to about 300°F to precipitate essentially only the aromatic carboxylic acid from the aqueous hydrolysis effluent;

separating the precipitated aromatic carboxylic acid from the aqueous hydrolysis effluent; and recycling aqueous hydrolysis effluent, subsequent to separation of the precipitated aromatic carboxylic acid, to the reactor.

2. The process of claim 1 wherein the catalyst is the ammonium salt of the aromatic carboxylic acid.

3. The process of claim 1 wherein the slurry is heated, prior to introduction into the reactor, by direct steam addition.

4. The process of claim 1 wherein the nitrile is a mononitrile and the carboxylic acid is a monocarboxylic acid.

5. The process of claim 1 wherein the nitrile is a polynitrile and the carboxylic acid is a polycarboxylic acid.

6. The process of claim 1 wherein the nitrile is a dinitrile and the carboxylic acid is a dicarboxylic acid.

7. The process of claim 6 wherein the dinitrile is terephthalonitrile and the carboxylic acid is terephthalic acid.

8. The process of claim 6 wherein the dinitrile is phthalonitrile and the carboxylic acid is phthalic acid.

9. The process of claim 6 wherein the dinitrile is isophthalonitrile and the carboxylic acid is isophthalic acid.

10. The process of claim 1 wherein the temperature of (a) is from about 350° to about 540°F.

* * * * *